(12) United States Patent
Siegel et al.

(10) Patent No.: US 7,914,825 B2
(45) Date of Patent: Mar. 29, 2011

(54) ENCAPSULATED VACCINIUM EXTRACTS WITH BALANCED GASTROINTESTINAL RELEASE

(75) Inventors: Sven Siegel, Höxter (DE); Elvira Mavric, Holzminden (DE); Gerhard Krammer, Holzminden (DE)

(73) Assignee: SYMRISE GmbH & Co. KG, Holzminden (DE)

( * ) Notice: Subject to any disclaimer, the term of this patent is extended or adjusted under 35 U.S.C. 154(b) by 146 days.

(21) Appl. No.: 12/186,883

(22) Filed: Aug. 6, 2008

(65) Prior Publication Data

US 2009/0041872 A1 Feb. 12, 2009

Related U.S. Application Data

(60) Provisional application No. 60/954,370, filed on Aug. 7, 2007.

(51) Int. Cl.
*A01N 65/00* (2009.01)

(52) U.S. Cl. ........................................ 424/725

(58) Field of Classification Search .................. None
See application file for complete search history.

(56) References Cited

U.S. PATENT DOCUMENTS

| | | | |
|---|---|---|---|
| 5,288,632 A | | 2/1994 | Pannell |
| 2006/0029711 A1 | * | 2/2006 | Theeuwen et al. ............ 426/573 |
| 2008/0255226 A1 | | 10/2008 | Eidenberger |

FOREIGN PATENT DOCUMENTS

| | | | |
|---|---|---|---|
| CN | 1974678 | * | 6/2007 |
| EP | 0242135 | | 4/1987 |
| EP | 0453316 | | 4/1991 |
| EP | 0566347 | | 4/1993 |
| EP | 1537789 | | 4/2003 |
| EP | 1454534 | | 9/2004 |
| JP | 2002335881 | * | 11/2002 |
| RU | 2257909 | | 12/2003 |
| WO | 9636433 | | 11/1996 |
| WO | WO-0128526 | | 4/2001 |
| WO | 200643858 | | 4/2006 |
| WO | 200683666 | | 8/2006 |

OTHER PUBLICATIONS

Database WPI Week 200340 Thomson Scientific, London, GB; AN 2003-424039, XP002501903 & JP 2002 335881 A (Yukijirushi Shokuhin KK) Nov. 26, 2002.

* cited by examiner

*Primary Examiner* — Michael V Meller
(74) *Attorney, Agent, or Firm* — Connolly Bove Lodge & Hutz LLP

(57) ABSTRACT

The invention relates to *Vaccinium* fruit extracts, related preparations, production methods and uses.

9 Claims, No Drawings

ENCAPSULATED VACCINIUM EXTRACTS WITH BALANCED GASTROINTESTINAL RELEASE

CROSS REFERENCE TO RELATED APPLICATIONS

This application claims the benefit of U.S. Provisional Application 60/954,370, filed Aug. 7, 2007. That application is hereby incorporated by reference in its entirety.

BACKGROUND OF THE INVENTION

Anthocyans are among the most important polyphenolic compounds in berries. They may be present in berries in an amount of up to 5000 mg/kg fresh weight. The aglycones (anthocyanidins) most commonly occurring in nature are: pelargonidin, cyanidin, delphinidin, peonidin, petunidin, malvidin. The anthocyanidins present in plants are glycosidically bound. Berries contain approximately 15 different anthocyans.

Anthocyans are found in particularly elevated concentration in the fruits (berries) of plants of the *Vaccinium* genus. The fruits of the blueberry (*Vaccinium myrtillus*) have a particularly high anthocyan content. The other species of the *Vaccinium* genus also have high contents of anthocyans. These include the North American highbush blueberry or cultivated blueberry (*Vaccinium corymbosum*), cowberry (*Vaccinium vitis-idaea*), common cranberry (*Vaccinium oxycoccos*), large cranberry or bearberry (*Vaccinium macrocarpon*), small cranberry (*Vaccinium microcarpum*), false berry (*Vaccinium gaultheroides*), bog blueberry (*Vaccinium uliginosum*), big huckleberry (*Vaccinium membranaceum*), red huckleberry (*Vaccinium parvifolium*), sparkleberry (*Vaccinium arboreum*), ohelo berry (*Vaccinium reticulatum*), and the Canadian blueberry (*Vaccinium myrtilloides*).

Anthocyans a capable of scavenging free radicals and stabilizing them by the conjugated double bond system, so interrupting free radical chain reactions. A protective function relative to proteins has been postulated. Polyphenols prevent or inhibit the formation of carbonyl compounds, which are capable of reacting with free amino groups and thus irreversibly modifying proteins. Polyphenols reduce lipid peroxidation and function as free-radical scavengers (*J. Agric. Food Chem.*, 2004, 52, 7419-7424: *Inhibition of protein and lipid oxidation in liposomes by berry phenolics*). This effect was confirmed unambiguously in vitro, the anthocyans of the blueberry (bilberry) proving the most effective, followed by raspberries, lingonberries and blackcurrants. Consumption of fresh strawberries (240 g), freeze-dried bilberries (100 g) and berry juices increases the antioxidative capacity of the blood plasma by up to 30% (*Current Nutr. & Food Sci.*, 2005, 1, 71-86: *Potential Health Benefits of Berries*).

The blueberry is known in natural medicine for its healing action in the case of diarrhea and gastrointestinal diseases, and is used in the widest possible range of medical fields, for example atherosclerosis, cataract, diabetes mellitus, diarrhea or retinopathy.

Polyphenols or anthocyans are also described in connection with cardiac conditions (CVD) and cancer. They are said to have a positive, preventative effect on the development of these diseases (*Antioxidant Activity of Plant Extracts Containing Phenolic Compounds, J. Agric. Food. Chem.*, 1999, 47, 3954-3962). In an in vitro study, phenolic extracts of different berries were tested for their action against the cell lines HT29 (intestinal cancer cells) and MCF7 (breast cancer cells). It has been demonstrated that all the extracts had a sequentially increasing inhibitory action on cell growth in concentrations of 0.025 to 0.5% (*J. Agric. Food Chem.*, 2004, 52, 7264-7271: *Inhibition of Cancer Cell Proliferation in Vitro by Fruit and Berry Extracts and Correlations with Antioxidant Levels*). Furthermore, it was possible to demonstrate that anthocyan-rich foodstuffs have a preventative action in vivo and in vitro on various types of cancer in the digestive tract (gastrointestinal tract) (oral, esophageal, intestinal, colorectal) (summarized in *J. Agric. Food Chem*, 2005, 53, 2859-2866: *Analysis of Anthocyanins in Rat Intestinal Contents-Impact of Anthocyanin Chemical Structure on Fecal Excretion*).

It is known from folk medicine that elderberry and cranberry extracts are used to alleviate urinary tract diseases. This action is likewise attributed to anthocyans.

Bioavailability

If it is to be possible to use anthocyans for medical purposes and for preventing gastrointestinal diseases, it is necessary to ensure the bioavailability of the anthocyans. This depends above all on how and to what extent they are absorbed and metabolized. The bioavailability of anthocyans is on average 0.5% when administered orally to humans (summarized in Fleschhut, J., *Untersuchungen zum Metabolismus, zur Bioverfügbarkeit und zur antioxidativen Wirkung von Anthocyanen* ("*Investigations into metabolism, bioavailability and antioxidative action of anthocyans*"), thesis, 2004). Compared with flavonoids, anthocyans have a very low bioavailability. The β-D-glycosidic form is of vital significance in terms of the bioavailability and kinetics of anthocyans (*J. Agric. Food Chem.*, 2006, 54, 583-589: *Fate of Anthocyanins and Antioxidant Capacity in Contents of the Gastrointestinal Tract of Weanling Pigs Following Black Raspberry Consumption; J. Agric. Food Chem*, 2005, 53, 2859-2866: *Analysis of Anthocyanins in Rat Intestinal Contents-Impact of Anthocyanin Chemical Structure on Fecal Excretion*). Beta-glucosidases, which are present in the body, cleave the glycosidic residues and form aglycones. Some studies show that, after oral administration, the glycosidic form of the anthocyans is absorbed (*Am. J. Clin. Nutr.*, 2001, 920-926: *Anthocyanins are absorbed in glycated forms in elderly women: a pharmacokinetic study*), but is also recovered in intact, unmodified form in urine and blood.

Absorption of individual anthocyans is determined by the chemical properties of the aglycone and of the sugar residue. Absorption of the anthocyans proceeds both in the stomach and in the small intestine (*Current Nutr. & Food Sci.*, 2005, 1, 71-86: *Potential Health Benefits of Berries*).

WO 96/36433 describes an encapsulation product with a shell, which is derived from microbial cell wall material. A substance is encapsulated which is not naturally present in the microbe. In addition, the shell is colored with a dye in such a way that the coloration is visible in the product. To produce the product, a grown, intact microbe is brought into contact with the substance to be encapsulated and a dye. The microbe is preferably alive at the beginning of the encapsulation process and their viability may be hindered for instance by irradiation. In any event, the microbe must be intact and must not be present in lysed form. The cell substance which has passed into solution during encapsulation is separated by centrifugation prior to drying.

U.S. Pat. No. 5,288,632 and EP 0 242 135 describe the production of a microbially encapsulated material in a grown, intact microbe with a lipid content of less than 40%, encapsulation proceeding in the absence of a plasmolyser or an organic lipid-extending substance. The microbe is present in grown form, i.e. it was recovered from the culture medium and is intact (not lysed). During production, the substance to be encapsulated diffuses through the cell wall and is retained passively within the microbe.

EP 0 453 316 describes a method of encapsulating lipophilic substances within yeast cells, whose intracellular components have been eluted by a heat treatment in the range of between 30 and 100° C. for at least one hour, in the presence of or in the absence of an elution promoter. The yeast extract is preferably isolated prior to contact with the lipophilic substance.

EP 1 454 534 describes microcapsules of microorganisms which have foreign substances encapsulated in the microorganisms and to whose surface saccharides, sweeteners, proteins and sugar alcohols are attached. In the method, first of all the foreign substances are incorporated into the microorganisms, and then the saccharides, sweeteners, proteins and sugar alcohols are attached. The attached substances bring about a modification of release behavior.

EP 0 566 347 describes the encapsulation of dyes in yeast ghosts. For this purpose, yeast debris is purified in a special process, so as then to encapsulate the dyes. During the process, the cell substances which escaped during autolysis are removed.

WO 2006/83666 describes encapsulation of a mixture consisting of 50 mg curcumin, 60 mg blueberry extract, 250 mg grapeseed extract, 375 mg green tea extract and 125 mg apple extract in gelatine capsules. Use thereof is described as a nutritional supplement for preventing and alleviating cardiovascular diseases and inflammatory processes.

WO 2006/43858 describes the use of mixtures of various plant extracts, containing for example cowberry (2-4%), for detoxifying cells, enhancing the antioxidative status of the body and stimulating intracellular biotransformation of xenobiotics. Use proceeds in the form of gelatine capsules.

RU 2 257 909 describes the use of blueberry extract with a flavonoid content of 5 wt. %. It is administered on a pharmaceutical carrier in the form of capsules, tablets, granules and the like. The product has a medical application.

EP 1 537 789 describes the microencapsulation of carotenes, tocopherols, extracts of *Passiflora incarnata*, (apigenin, luteolin, or the corresponding glycosides) and extracts of *Vaccinium myrtillus* (delphinidin). The shell may consist of natural, semi-synthetic or synthetic materials. Natural shell materials are for example gum arabic, agar-agar, agarose, maltodextrins, alginic acid or the salts thereof, for example sodium or calcium alginate, fats and fatty acids, cetyl alcohol, collagen, chitosan, lecithins, gelatin, albumin, shellac, polysaccharides, such as starch or dextran, polypeptides, protein hydrolysates, sucrose and waxes. Semi-synthetic shell materials are inter alia chemically modified celluloses, in particular cellulose esters and ethers, for example cellulose acetate, ethylcellulose, hydroxypropylcellulose, hydroxypropylmethylcellulose and carboxymethylcellulose, and starch derivatives, in particular starch ethers and esters. Synthetic shell materials are for example polymers such as polyacrylates, polyamides, polyvinyl alcohol or polyvinylpyrrolidone.

DISCUSSION OF THE PRIOR ART

Many of the encapsulation products described in the prior art exhibit a release characteristic which leads either to release of the active ingredients only in the stomach or only in the intestine. For instance, very readily water-soluble carriers lead generally to immediate release of the active ingredients in the mouth or stomach. After release, the active ingredients are immediately exposed to breakdown processes or are in part bound irreversibly to proteins. They are then no longer available in the intestine. On the other hand, encapsulated products which are intended to be released in the intestine are made in such a way that they do not release the active ingredients in the stomach and do not have any effect therein. However, for the purposes of maintaining health and preventing disease, it would be advantageous for the anthocyan-containing extracts to be released continuously both in the stomach and in the intestine.

The encapsulation of anthocyan-containing extracts in yeasts is associated with problems according to the prior art. It is important for encapsulation for some of the cell contents to be broken down and dissolved by the action of cell's endogenous enzymes. When live yeasts come into contact with the anthocyan-containing extracts, the enzymes important for autolysis are inactivated or inhibited and breakdown of the cell substance does not take place to the desired extent. The anthocyan-containing extracts therefore remain predominantly on the surface of the cells and are insufficiently encapsulated. The prior art further discloses encapsulation methods and products produced therewith, in which the yeasts are eluted or autolysed prior to contact with the substances to be encapsulated, the extract which has escaped from the cells being removed prior to contact with the substances to be encapsulated. The encapsulation products obtained in this way do indeed exhibit release in the stomach, but release in the intestine is very limited.

According to the prior art, for yeast encapsulation the substances to be encapsulated are retained inside the yeast cell.

It was therefore the object of the invention to provide a preparation (encapsulation product) for anthocyans which allows uniform or controllable release of the anthocyans in the stomach and intestine of a mammal, in particular of a human. The preparation should be as simple and economic as possible to produce.

SUMMARY OF THE INVENTION

According to the invention, therefore, in particular a *Vaccinium* fruit extract is provided, comprising:
a) a *Vaccinium* fruit extract,
b) a fraction of water-insoluble constituents of a yeast cell lysate, and
c) a fraction of water-soluble constituents of a yeast cell lysate.

The inventors assume that the *Vaccinium* fruit extract is reversibly bound to the water-soluble constituents of the yeast cell lysate, and it is furthermore suspected that the *Vaccinium* fruit extract and the water-soluble constituents of the yeast cell lysate are attached to the surface of the insoluble cell residues. Release of the encapsulated *Vaccinium* fruit extract, in particular of the blueberry extract, takes place in suitable embodiments in balanced manner in the stomach and in the intestine.

A method is additionally provided for producing the encapsulation product according to the invention, as is the use thereof in foodstuffs.

The production method comprises the steps:
a) providing a *Vaccinium* fruit extract,
b) providing a fraction of water-insoluble constituents and a fraction of water-soluble constituents of a yeast cell lysate, and
c) mixing the *Vaccinium* fruit extract with the yeast cell lysate and water at a temperature of between 0 and 60° C. for a period of up to 4 hours, preferably of between 6 and 30 min.

According to the invention, encapsulation products are preferably used in foodstuffs and pharmaceutical products.

DETAILED DESCRIPTION OF THE PREFERRED EMBODIMENTS

It has surprisingly been found that the preparation according to the invention (the encapsulation product according to the invention) releases *Vaccinium* fruit extracts very effectively both in the stomach and in the intestine. Furthermore, release takes place in a balanced ratio in the stomach and in the intestine. This release characteristic is surprising, since the encapsulation of *Vaccinium* fruit extracts in insoluble cell residues alone or in soluble constituents of the yeast lysate alone in each case leads only to major release in the stomach. Release in the intestine takes place in both cases only with very great delay. Only by combining the insoluble cell residue, the soluble fraction of the yeast lysate and the *Vaccinium* fruit extracts is the desired release characteristic achieved. The encapsulation product according to the invention is distinguished over the general prior art in that the *Vaccinium* fruit extracts are not present in a bound state inside the yeast cell residue, but rather are bound reversibly to the soluble constituents of the yeast cell lysate and attached to the surface of the insoluble cell residues.

Of advantage, in addition to the specific release characteristic, are the simplicity of the production method for preparations according to the invention (encapsulation products) due to the absence of a coating requiring separate application and the high level of environmental friendliness of the method, since no waste arises during encapsulation. In addition, the encapsulation step may be performed within the shortest possible time, such that the valuable ingredients of the *Vaccinium* fruit extract are not subject to or are subject to only slight breakdown reactions.

For the purposes of the present invention, a yeast extract or yeast cell lysate is a lysate of yeast cells, in particular as described further below, which comprises water-insoluble as well as water-soluble constituents. The water-soluble constituents are here characterized by their solubility in water. They escape from the cell during autolysis and are predominantly present in the aqueous medium which surrounds the cells. The water-soluble constituents generally comprise a mixture of water-soluble proteins, peptides, free amino acids, carbohydrates, nucleic acid breakdown products, organic acids and lipid breakdown products. Water-soluble constituents are in particular:

- the free amino acids threonine, serine, asparagine, glutamic acid, proline, cysteine, glycine, alanine, citrulline, valine, cystine, methionine, isoleucine, leucine, tyrosine, phenylalanine, homocystine, ornithine, lysine, histidine, arginine and the dipeptides, oligopeptides (3-10 amino acid residue molecules) and polypeptides (11-100 amino acid residue molecules) and water-soluble proteins (more than 100 amino acid residue molecules) formed therefrom;
- glucose and water-soluble di-, tri-, oligo- and polysaccharides built up therefrom;
- nucleosides and nucleotides such as adenosine monophosphate, guanosine monophosphate, uracil monophosphate;
- propionic acid, succinic acid, maleic acid, formic acid, acetic acid, oxalic acid, citric acid, tartaric acid, and lactic acid and
- glycerol.

The water-insoluble constituents consist of substantially intact cell walls and further cellular constituents, which are not in a water-soluble form after autolysis.

These further, water-insoluble constituents include in particular fragments of the cell membrane, the cell nucleus, the RNA and DNA, the mitochondria and lipids and the water-insoluble breakdown products of the lipids.

An encapsulation product according to the invention preferably comprises:
a) 0.5-50.0 wt. % *Vaccinium* fruit extract,
b) 30-98.9 wt. % yeast cell lysate (comprising a fraction of water-insoluble constituents of a yeast cell lysate and a fraction of water-soluble constituents of a yeast cell lysate),
c) 0.1-10.0 wt. % sodium chloride,
d) 0.1-10.0 wt. % residual water.

Preferably, the encapsulation product according to the invention comprises or consists of:
a) 10.0-30.0 wt. % *Vaccinium* fruit extract,
b) 51.0-89.4 wt. % yeast cell lysate
c) 0.5-9.0 wt. % sodium chloride
d) 0.1-10.0 wt. % residual water.

Particularly preferably, the encapsulation product according to the invention comprises or consists of:
a) 15.0-25.0 wt. % *Vaccinium* fruit extract,
b) 57.0-84.4 wt. % yeast cell lysate
c) 0.5-8.0 wt. % sodium chloride
d) 0.1-10.0 wt. % residual water.

The term *Vaccinium* fruit extract comprises the generally colored, predominantly water-soluble extract of the fruits (berries) of the North American highbush blueberry or cultivated blueberry (*Vaccinium corymbosum*), cowberry (*Vaccinium vitis-idaea*), common cranberry (*Vaccinium oxycoccos*), large cranberry or bearberry (*Vaccinium macrocarpon*), small cranberry (*Vaccinium microcarpum*), false berry (*Vaccinium gaultheroides*), bog blueberry (*Vaccinium uliginosum*), big huckleberry (*Vaccinium membranaceum*), red huckleberry (*Vaccinium parvifolium*), sparkleberry (*Vaccinium arboreum*), ohelo berry (*Vaccinium reticulatum*), and the Canadian blueberry (*Vaccinium myrtilloides*). For the purposes of the present invention, the extract of the blueberry (bilberry) is particularly preferred.

These extracts are insoluble or only very slightly soluble in fat or oil. The valuable constituents include the anthocyans, which make up a fraction of preferably 0.1-30 wt. % of the dry extract. The fraction of anthocyans in the preparations according to the invention amounts preferably to 0.125-12.5 wt. %, preferably 2.5-7.5 wt. % and particularly preferably 3.75-6.25 wt. %. The anthocyans cyanidin, delphinidin, malvidin, petunidin, peonidin occurring in the *Vaccinium* genus are present, predominantly glycosidically bound, as cyanidin 3-arabinoside, cyanidin 3-galactoside, cyanidin 3-glucoside, delphinidin 3-arabinoside, delphinidin 3-galactoside, delphinidin 3-glucoside, malvidin 3-arabinoside, malvidin 3-galactoside, malvidin 3-glucoside, petunidin 3-arabinoside, petunidin 3-galactoside, petunidin 3-glucoside, peonidin 3-arabinoside, peonidin 3-galactoside, peonidin 3-glucoside. Further ingredients of the extract which may be mentioned are above all saccharides, organic acids, and further polyphenols, such as flavonoids and tannic acids (tannins) and vitamins.

The *Vaccinium* fruit extract may be obtained from the fruits (berries) of the plants using per se known extraction methods. These include, for example, maceration or percolation. Water and ethanol or mixtures thereof may be used as the extraction medium, for example. Instead of ethanol, methanol and other water-soluble solvents may also be used. The selected temperature and mechanical disintegration of the fruit may assist extraction. Mechanical disintegration of the fruit, for example by stirrers, homogenizers or ultrasound, is also recommended in the prior art. In addition, further extraction-promoting substances, such as acids, bases and enzymes, may be used. The extract may without further treatment be added in a thickened or dried state to the lysed yeast suspension.

The yeasts are preferably selected from among Ascomycetes (sac fungi), with the Saccharomycetaceae family, the Saccharomycetoideae subfamily and the *Saccharomyces* genus or the Cryptococcaceae family and its *Candida*, *Torulopsis* and *Kloeckera* genera being preferred. Examples thereof are *Saccharomyces carlsbergensis*, *Saccharomyces bayanus* and *Saccharomyces uvarum*. Because of very good availability and production in technically relevant quantities, the use of *Saccharomyces cerevisiae* (also known as baker's yeast or brewer's yeast) and *Candida utilis* (also known as *Torula* yeast and previously as *Torulopsis utilis* or *Torula utilis*) may in particular be considered.

For the purposes of the present invention, autolysed yeast is the product of incomplete yeast autolysis. Yeast autolysis is known in the prior art and denotes breakdown of the yeasts by their own enzymes. It is carried out by leaving an aqueous yeast suspension to itself at a temperature of between approx. 40 and 65° C. for a period of approx. one hour up to approx. 4 days. During this time, the cell's endogenous enzymes bring about breakdown and allow dissolution of the cell constituents. Autolysis may be assisted by the use of plasmolysers, acids, bases, non-endogenous enzymes and organic solvents. Use of these auxiliary substances is likewise described in the prior art. Particular emphasis should be laid on the use of sodium chloride (common salt) as a plasmolyser. It is added at the beginning to the yeast suspension and brings about diffusion of the water into the interior of the cell through the semipermeable cell membrane, which at this point is still intact.

In the course of autolysis, the cell membrane is damaged in such a way that the dissolved cell constituents can pass into the surrounding aqueous medium. However, complete breakdown (complete autolysis) of the cells is not the aim of the invention. Instead, it is an explicit part of the invention that the cell is only dissolved in part (incompletely) and insoluble cell residues and soluble constituents arise as products of the autolysis. An important constituent of the insoluble cell residues are substantially intact cell walls, which enclose the residual undissolved constituents. Both the insoluble cell residues and the water-soluble constituents may be used according to the invention in the encapsulation product. The ratio of water-insoluble constituents to soluble constituents preferably amounts to 0.1:1 to 9:1, particularly preferably 0.4:1 to 2.3:1 and particularly preferably 0.7:1 to 1.5:1.

The properties according to the invention of the product include balanced release of the *Vaccinium* fruit extracts in the stomach and in the intestine. Balanced release in the stomach and in the intestine is understood for the purposes of the present invention to mean a ratio of gastric release to intestinal release of 0.3:1 to 3:1, preferably 0.4:1 to 2.5:1 and particularly preferably 0.5:1 to 2:1. Gastric or intestinal release takes place in accordance with the following in vitro digestive test according to *Analyst*, 2002, 127, 1638-1641: *Development of a sequential enzymolysis approach for the evaluation of the bioaccessibility of Cd and Pb from cocoa.*

The following solutions are used as digestive juices:

| "Artificial saliva" | |
|---|---|
| 5.0 g | potassium hydrogencarbonate |
| 0.64 g | potassium chloride |
| 0.15 g | sodium carbonate |
| 20.61 mg | α-amylase |
| 100 mg | mucin |
| in 1000 ml | dist. water | adjust pH value to 6.9 with NaOH

| "Gastric juice" | |
|---|---|
| 1 g | pepsin |
| 0.88 g | sodium chloride |
| in 100 ml | dist. water | adjust pH value to 2.5 with HCl

| "Intestinal juice" | |
|---|---|
| 30 mg | KCl |
| 50 mg | $CaCl_2$ |
| 20 mg | $MgCl_2$ |
| 20 mg | $NaHCO_3$ |
| 30 mg | trypsin |
| 900 mg | pancreatin |
| 900 mg | bile, freeze-dried |
| in 100 ml | dist. water | adjust pH value to 6.9 with NaOH 1 g of the encapsulation product is combined with 6.25 g of "artificial saliva" with constant stirring and incubated for 15 min at 37° C. The pH value of the solution is adjusted to 2.5 with dilute hydrochloric acid. 20 ml of the "artificial gastric juice" are added thereto and the mixture is incubated with stirring for 4 h at 37° C. To determine release of the anthocyans in the stomach, 5 g are taken from this solution and determined by means of RP-HPLC with UV detection. Once the pH value has been adjusted to 6.9, 10 ml of the "intestinal juice" are added and the mixture is incubated with stirring for a further 3 h at 37° C. Then the enzymatic reaction is stopped by adjusting the pH value to pH 2.5 with dilute hydrochloric acid. 5 g of the specimen adjusted in this way are used to determine intestinal release by RP-HPLC.

For comparison or for quantitative evaluation of the release of anthocyans from the encapsulated bilberry extract during the digestive process in vitro, a 20% aqueous solution of the unencapsulated bilberry extract was measured as standard by means of RP-HPLC with UV detection. Assuming that this aqueous solution corresponds to 100% release in the stomach or in the intestine, the release of anthocyans from the encapsulated bilberry extract in the gastrointestinal tract was calculated (see Table 1).

The invention further relates to a method of producing such an encapsulation product:

a) providing a *Vaccinium* fruit extract, b) providing a fraction of water-insoluble constituents and a fraction of water-soluble constituents of a yeast cell lysate, and c) mixing the *Vaccinium* fruit extract with the yeast cell lysate fractions and water at a temperature of between 0 and 60° C. for a period of less than 4 hours, preferably between 6 and 30 min.

Optionally, the mixture produced in step c) is dried.

The mixture produced in step c) comprises or preferably consists of:
a) 0.2-17.0 wt. % *Vaccinium* fruit extract,
b) 10.0-33.0 wt. % yeast cell lysate (comprising a fraction of water-insoluble constituents of a yeast cell lysate and a fraction of water-soluble constituents of a yeast cell lysate),
c) 0.1-3.0 wt. % sodium chloride,
d) 47.0-89.7 wt. % water.

The mixture produced in step c) comprises or preferably consists of:
a) 3.0-10.0 wt. % *Vaccinium* fruit extract,
b) 17.0-30.0 wt. % yeast cell lysate
c) 0.2-3.0 wt. % sodium chloride
d) 57.0-79.8 wt. % water.

The mixture produced in step c) comprises or preferably consists of:
a) 5.0-8.0 wt. % *Vaccinium* fruit extract,
b) 19.0-28.0 wt. % yeast cell lysate
c) 0.2-3.0 wt. % sodium chloride
d) 61.0-75.8 wt. % water.

The batch may be mixed using per se known equipment, such as stirrers, rotor-stator dispersers or high pressure homogenizers. Preferably, the mixing period amounts to between 6 and 20 min and particularly preferably between 6 and 15 min. Mixing preferably takes place at temperatures of between 10 and 60° C. Particularly preferably, the mixture is heated from 15 to 50° C. Mixing proceeds until the *Vaccinium* fruit extract is reversibly bound to the water-soluble constituents of the yeast cell lysate, but has preferably not penetrated inside the insoluble cell residue.

Drying proceeds with known drying methods, such as for example spray drying, fluidized bed spray granulation, belt drying, vacuum drying or freeze drying.

Spray drying is preferably used, air inlet temperatures regularly being used in the range from 120 to 300° C., preferably in the range from 150 to 250° C. and particularly preferably in the range from 180 to 220° C.

The air outlet temperatures are regularly in the range from 50 to 150° C., preferably in the range from 60 to 120° C. and particularly preferably in the range from 70 to 100° C. Any desired type of atomizer may be used for this purpose, such as for example nozzles, mechanical atomizers and ultrasound atomizers.

Nozzles which may, for example, be used are single-fluid nozzles, pressure nozzles, solid cone pressure nozzles, hollow cone spray nozzles, two-fluid nozzles, three-fluid nozzles and four-fluid nozzles etc. Mechanical atomizers (rotary atomizers) comprise a rotating body which breaks the spray mixture up into small drops. The rotating bodies are conventionally disks or also bells; a disk atomizer is one example of a mechanical atomizer. Suitable atomizers may be selected by a person skilled in the art in particular depending on the amount of spray mixture to be dried and the size of the anticipated aroma particles. Rotary atomizers and in particular disk atomizers are used as preferred atomizers. When using spray drying, an encapsulation product with a particle size of between 2 and 150 µm arises as a function of the equipment and the parameters used. Using the other stated drying methods, particles of up to as much as 5 mm in size may arise.

For the purposes of the present invention, further substances may be added to the composition according to the invention prior to drying. These include in particular saccharides including starches, modified starches, maltodextrin, dextrose syrup, starch octenylsuccinate, sucrose, dextrose, gum arabic, cellulose derivatives; and sweeteners, proteins and sugar alcohols.

Preparations according to the invention serving for nutrition or pleasure and containing one or more encapsulation products according to the invention are preferably selected from:

bakery products (for example bread, dry cookies, cakes, muffins, wafers, cake mixes, other pastry products), confectionery (for example white, milk or dark chocolate, filled chocolates (for example with aromatized fondant mass, of the After Eight type), chocolate bars, other bar products, chewable candies, fruit gums, hard and soft caramels, chewing gum, sugar pearls, lollipops), capsules (preferably seamless capsules for direct consumption, preferably with an envelope based on gelatin and/or alginate), fatty masses (for example bakery product fillings for example cookie fillings, chocolate fatty fillings, bar product fatty fillings), sprinkling mixtures (toppings), alcoholic or non-alcoholic beverages, (for example coffee, tea, wine, beverages containing wine, beer, beverages containing beer, liqueurs, spirits, brandies, fruit-containing carbonated beverages, isotonic beverages, soft drinks, nectars, fruit and vegetable juices, fruit and vegetable juice preparations), instant beverages or instant powders (for example instant cocoa beverages, instant tea beverages, instant coffee beverages, instant desserts in powder form such as blancmange powder or jelly), meat products (for example ham, fresh or cured sausage preparations, spiced or marinated fresh or cured meat products), eggs or egg products, (for example dried egg powder), cereal products and/or nut products (for example breakfast cereals, cornflakes, porridge oats, bagged muesli, muesli bars, trail mix, sweet popcorn, nut bars, fruit and nut bars, precooked ready rice products), dairy products (for example milk beverages, milk ice cream, yogurt, blancmange, kefir, curd cheese, soft cheese, hard cheese, dried milk powder, whey, butter, buttermilk, partially or fully hydrolysed milk protein-containing products), products made from soy protein or other soybean fractions (for example soy milk and products made therefrom, soy lecithin-containing preparations, fermented products such as tofu or tempe or products made therefrom, soy sauces), fruit preparations (for example jams, fruit ice cream, fruit sauces, fruit fillings), vegetable preparations, (for example ketchup, sauces, dried vegetables, deep-frozen vegetables, precooked vegetables, pickled vegetables, preserved vegetables), snack articles (for example baked or fried potato chips or potato dough products, bread dough products, corn- or peanut-based extrudates), fat- or oil-based products or corresponding emulsions thereof (for example mayonnaise, remoulade, dressings, seasoning preparations), other ready-to-serve meals and soups (for example dried soups, instant soups, precooked soups), spices, seasoning mixtures and in particular powdered seasonings, which are for example used in snack food applications.

The total proportion of encapsulation products according to the invention in a preparation according to the invention serving for nutrition or pleasure preferably lies in the range from 0.1 to 10 wt. %, preferably in the range from 0.25 to 5 wt. %, and particularly preferably in the range from 0.5 to 3 wt. %, in each case relative to the total mass of the preparation.

Preparations according to the invention serving for nutrition or pleasure may also be nutritional supplements in the form of capsules, tablets (uncoated and coated tablets, for example coatings resistant to gastric juices), sugar-coated tablets, granules, pellets, mixtures of solids, dispersions in liquid phases, as emulsions, as powders, as solutions, as pastes or as other swallowable or chewable preparations.

Preferred preparations according to the invention serving for nutrition or pleasure are:
confectionery such as for example hard candies, chewing gums, fruit gums, chewable candies, sugar-coated (refreshing) lozenges, compressed lozenges, hard caramels, chocolate spreads, candies and chocolate, bakery products such as cakes, wafers and cookies, snacks, instant meals and other instant products (soups, sauces, beverage powders and granules, tea bags, seasoning mixtures), ice cream, fruit preparations, (marmalades, jams, fruit sauces), desserts (blancmange, jelly), dairy products (quark, yogurt, milk drinks, whey preparations) and cereals (cornflakes, muesli bars). In addition, use is also advantageous in nutritional supplements and pharmaceutical products, such as suckable tablets, throat or cough drops, pharmaceutical powders, tablets or granules.

The snacks according to the invention mostly comprise salty snacks, such as for example potato/corn chips, extrudates pellets, popcorn, crackers, lye rolls and fried or oven-baked dough products. Encapsulation products according to the invention or an aroma composition comprising the encapsulation products according to the invention may be incorporated into a snack article or applied thereto. Incorporation or application may be achieved by means of powdered seasoning, sprayed-on oil slurry, fatty fillings or dough aromatization.

Further constituents which may be used for preparations according to the invention serving for nutrition or pleasure are conventional basic and auxiliary substances and additives for foodstuffs or products consumed for pleasure, for example water, mixtures of fresh or processed, plant or animal basic or raw materials (for example raw, roasted, dried, fermented, smoked and/or boiled meat, bone, cartilage, fish, vegetables, fruit, herbs, nuts, vegetable or fruit juices or pastes or mixtures thereof), digestible or indigestible carbohydrates (for example amylose, amylopectin, inulin, xylans, cellulose), natural or hardened fats (for example tallow, lard, palm fat, coconut oil, hardened vegetable fat), oils (for example sunflower oil, peanut oil, corn germ oil, olive oil, fish oil, soy oil, sesame oil), fatty acids or the salts thereof (for example potassium stearate), proteinogenic or non-proteinogenic amino acids and related compounds (for example γ-aminobutyric acid, taurine), peptides (for example glutathione), native or processed proteins (for example gelatin), enzymes (for example peptidases), nucleic acids, nucleotides, taste-correcting agents for unpleasant taste impressions, further taste modulators for further, generally not unpleasant taste impressions, other taste-modulating substances (for example inositol phosphate, nucleotides such as guanosine monophosphate, adenosine monophosphate or other substances such as sodium glutamate or 2-phenoxypropionic acid), emulsifiers (for example lecithins, diacylglycerols, gum arabic), stabilizers (for example carageenan, alginate), preservatives (for example benzoic acid, sorbic acid), antioxidants (for example tocopherol, ascorbic acid), chelating agents (for example citric acid), organic or inorganic acidulants (for example malic acid, acetic acid, citric acid, tartaric acid, phosphoric acid), bitter substances (for example quinine, caffeine, limonin, amarogentin, humolone, lupolone, catechins, tannins), mineral salts (for example sodium chloride, potassium chloride, magnesium chloride, sodium phosphates), substances preventing enzymatic browning (for example sulfite, ascorbic acid), essential oils, plant extracts, natural or synthetic dyes or coloring pigments (for example carotenoids, flavonoids, anthocyans, chlorophyll and the derivatives thereof), spices, trigeminally active substances or plant extracts containing such trigeminally active substances, cooling active ingredients such as for example menthol, menthol derivatives (for example L-menthol, L-menthyl lactate, L-menthyl glutarate, L-menthyl succinate) or cubebol, synthetic, natural or nature-identical aroma substances or odoriferous substances and odor-correcting agents.

Preparations according to the invention serving for nutrition or pleasure may additionally contain one or more taste-correcting agents, preferably selected from the following list: nucleotides (for example adenosine 5'-monophosphate, cytidine 5'-monophosphate) or the pharmaceutically acceptable salts thereof, lactisole, sodium salts (for example sodium chloride, sodium lactate, sodium citrate, sodium acetate, sodium gluconate), further hydroxyflavanones (for example eriodictyol, homoeriodictyol or the sodium salts thereof), in particular according to US 2002/0188019, hydroxybenzoic acid amides according to DE 10 2004 041 496 (for example 2,4-dihydroxybenzoic acid vanillylamide, 2,4-dihydroxybenzoic acid N-(4-hydroxy-3-methoxybenzyl)amide, 2,4,6-trihydroxybenzoic acid N-(4-hydroxy-3-methoxybenzyl)amide, 2-hydroxybenzoic acid N-4-(hydroxy-3-methoxybenzyl)amide, 4-hydroxybenzoic acid N-(4-hydroxy-3-methoxybenzyl)amide, 2,4-dihydroxybenzoic acid N-(4-hydroxy-3-methoxybenzyl)amide monosodium salt, 2,4-dihydroxybenzoic acid N-2-(4-hydroxy-3-methoxyphenyl)ethylamide, 2,4-dihydroxybenzoic acid N-(4-hydroxy-3-ethoxybenzyl)amide, 2,4-dihydroxybenzoic acid N-(3,4-dihydroxybenzyl)amide and 2-hydroxy-5-methoxy-N-[2-(4-hydroxy-3-methoxyphenyl)ethyl]amide (aduncamide), 4-hydroxybenzoic acid vanillylamide), bitterness-masking hydroxydeoxybenzoins according to WO 2006/106023 and the documents based thereon (Symrise) (for example 2-(4-hydroxy-3-methoxyphenyl)-1-(2,4,6-trihydroxyphenyl)ethanone, 1-(2,4-dihydroxyphenyl)-2-(4-hydroxy-3-methoxyphenyl)ethanone, 1-(2-hydroxy-4-methoxyphenyl)-2-(4-hydroxy-3-methoxyphenyl)ethanone), amino acids (for example gamma-aminobutyric acid according to WO 2005/096841 for reducing or masking an unpleasant taste impression such as bitterness), malic acid glycosides according to WO 2006/003107, salty tasting mixtures according to WO 2007/045566, diacetyl trimers according to WO 2006/058893, divanillin, mixtures of whey proteins with lecithins and/or bitterness-masking substances such as gingerdione according to WO 2007/003527.

Preparations according to the invention serving for nutrition or pleasure may additionally contain one or more alkamides, preferably selected from the group consisting of: 2E,4E-decadienoic acid N-isobutylamide (pellitorine), 2E,4Z-decadienoic acid N-isobutylamide (cis-pellitorine), 2Z,4Z-decadienoic acid N-isobutylamide, 2Z,4E-decadienoic acid N-isobutylamide, 2E,4E-decadienoic acid N-([2S]-2-methylbutyl)amide, 2E,4E-decadienoic acid N-([2S]-2-methylbutyl)amide, 2E,4E-decadienoic acid N-([2R]-2-methylbutylamide), 2E,4Z-decadienoic acid N-(2-methylbutyl)amide, 2E,4E-decadienoic acid N-piperide (achilleamide), 2E,4E-decadienoic acid N-piperide (sarmentine), 2E-decenoic acid N-isobutylamide, 3E-decenoic acid N-isobutylamide, 3E-nonenoic acid N-isobutylamide, 2E,6Z,8E-decatrienoic acid N-isobutylamide (spilanthol), 2E,6Z,8E-decatrienoic acid N-([2S]-2-methylbutyl)amide (homospilanthol), 2E,6Z,8E-decatrienoic acid N-([2R]-2-methylbutyl)amide, 2E-decen-4-ynoic acid N-isobutylamide, 2Z-decen-4-ynoic acid N-isobutylamide (sanshool).

Although the release characteristic of the encapsulation products according to the invention is tailored to release in the digestive tract, they may be constituents of products which are not intended for swallowing and digesting by humans, for example consumer articles such as personal hygiene products, household products, tobacco products (for example cigarettes), cosmetics (face masks) and of oral care products such as toothpastes, tooth gels, tooth creams, dental care chewing gums and mouthwashes.

The invention is illustrated by way of example by means of the following Examples. Unless otherwise stated, all stated values relate to weight.

Example 1

Encapsulation Product According to the Invention 300 g of fresh baker's yeast (Vital Gold made by Deutsche Hefewerke GmbH Nürnberg) and 10 g of common salt (sodium chloride) are mixed in a beaker with a wooden spoon. As a result of plasmolysis, the yeast mass becomes a relatively low-viscosity suspension. The suspension is placed in a water bath at a temperature of 60° C., left to stand, covered, for 3 hours and stirred from time to time with a spoon. In the process, autolysis takes place and from the initially live, intact yeast there arise the insoluble cell residues and the water-soluble constituents of the yeast cell lysate. The batch is cooled to 20° C. in the cold water bath. 37.5 g of blueberry extract (bilberry extract made by Kaden Biochemicals GmbH, Hamburg, Germany) are added and dispersed for 10 min with an Ultra Turrax. The suspension is fed to a Niro Minor spray tower with a disk atomizer. The air inlet temperature amounts to 200° C. and the air outlet temperature amounts to 80° C.

Example 2

Encapsulation Product According to the Invention 500 g of Springer (R) 2000 (dried autolysed yeast including insoluble cell residues and soluble yeast extract made by Bio Springer, Maisons-Alfort Cedex, France) are suspended in 1500 g of water. 125 g of blueberry extract (bilberry extract made by Kaden Biochemicals GmbH, Hamburg, Germany) are added. The batch is dispersed for 10 min at 3000 rpm with an Ultra Turrax. It is heated in the process from 18 to 49° C. The suspension is fed to a Niro Minor spray tower with a disk atomizer. The air inlet temperature amounts to 200° C. and the air outlet temperature amounts to 80° C. The encapsulation product according to the invention is obtained having a blueberry extract content of 20% and a particle size of 12 µm.

When examined under a microscope at 1200× magnification (after suspension in distilled water), the insoluble cell residue with the substantially intact cell wall is visible. It encloses the residues of the virtually uncolored remaining cell substance. This indicates that the remaining cell substance inside the cell does not perform any significant encapsulation function. Only the cell wall appears red-bluish in color, due to the attachment of the blueberry extract in combination with the soluble yeast extract (water-soluble constituents of the yeast cell lysate).

Example 3

Comparative Example, not According to the Invention 500 g of Springer (R) 2000 from Example 2 are suspended in 1500 g of water (20° C.). The insoluble cell residues are separated from the water-soluble constituents by means of filtration through a paper filter and dried at 40° C. in a circulating air drying cabinet. The resultant soluble yeast extract (undersize) is likewise dried at 40° C. in the circulating air drying cabinet, further processing being described in Example 4.

The insoluble cell residues (192 g) were suspended in 576 g of water and 48 g of blueberry extract from Example 1 were added and dispersed for 10 min with an Ultra Turrax at 3000 rpm. Drying proceeded as in Example 1.

When examined under a microscope at 1200× magnification, the insoluble cell residue with the substantially intact cell wall is visible. It encloses the residues of the red-bluish-colored remaining cell substance. This indicates that the encapsulation function is mainly carried out by the remaining cell substance inside the cell.

Example 4

Comparative Example, not According to the Invention

The soluble yeast extract (296 g) from Example 3 was dissolved in 888 g of water and then combined with 74 g of the blueberry extract from Example 1. Treatment with the Ultra Turrax and drying are performed as in Example 1.

Example 5

Digestion Test

Examples 2 to 4 were used in the above-described in vitro digestion test and the results are reproduced in the Table.

TABLE 1

In vitro release of the anthocyans according to the digestion test

| Example | Description | Release of anthocyans in the stomach [%]* | Release of anthocyans in the intestine [%]* |
|---|---|---|---|
| 2 | According to the invention | 21.97 | 23.9 |
| 3 | Comparison | 25.7 | 5.2 |
| 4 | Comparison | 30.5 | 11.2 |

*relative to the total content of anthocyans in the encapsulation product

As Table 1 reveals, in all the tested encapsulation forms the anthocyans are released very effectively in the stomach. In Example 2 according to the invention, however, it is clear that release in the stomach takes place to a lesser extent than in comparative examples 3 and 4. This is unexpected, since the composition of Example 2 according to the invention is actually only a mixture of Examples 3 and 4, on the basis of which, in Example 2 release in the stomach of between 25.7 and 30.5% would have been expected.

At 23.9%, release in the intestine is at its greatest in the Example according to the invention. This characteristic is also unexpected, since actually release of between 5.2 and 11.2% would have been expected.

Example 6

Spray-Dried Encapsulation Products According to the Invention with Further Carriers

| | Preparation (quantity used in wt. %) | | | |
|---|---|---|---|---|
| Constituent | A | B | C | D |
| Drinking water | 65% | 65% | 65% | 65% |
| Maltodextrin with dextrose equivalent 20 | 8% | 0% | 4% | 6% |
| Gum arabic | 0% | 8% | 4% | 2% |
| Yeast, Springer (R) 2000 | 20% | 20% | 20% | 20% |
| Blueberry extract | 7% | 7% | 7% | 7% |

The respective preparation is introduced into a suitable mixing vessel and mixed for 10 min with an Ultra Turrax at 3000 rpm. The procedure then proceeds as indicated in Example 2. The product according to the invention is obtained, with fractions of further carriers.

Example F1

Chewing Gums with Encapsulation Products According to the Invention

Chewing gum base K2 consisted of 28.5% terpene resin, 33.9% polyvinyl acetate (MW=14000), 16.25% hydrogenated vegetable oil, 5.5% mono- and diglycerides, 0.5% polyisobutene (MW 75000), 2.0% butyl rubber (isobutene/isoprene copolymer), 4.6% amorphous silicon dioxide (water content approx. 2.5%), 0.05% antioxidant tert.-butyl hydroxytoluene (BHT), 0.2% lecithin, and 8.5% calcium carbonate. Chewing gum base K2 and the chewing gums may be produced in a similar manner to U.S. Pat. No. 6,986,907.

| | I (Wt. %) | II (Wt. %) | III (wt. %) |
|---|---|---|---|
| Chewing gum base K2 | 25.30 | 27.30 | 26.30 |
| Sorbitol | ad 100 | ad 100 | ad 100 |
| Glycerol | 2.40 | 2.40 | 2.40 |
| Lecithin | 7.00 | 7.00 | 7.00 |
| Aspartame | 0.14 | 0.14 | 0.14 |
| Encapsulated aspartame | 0.68 | 0.68 | 0.48 |
| Menthol, spray-dried | 1.00 | 0.50 | 0.40 |
| Cherry aroma, spray-dried | — | 1.20 | — |
| Lemon aroma | 1.10 | 1.30 | 1.68 |
| Orange oil, natural | 0.40 | — | — |
| Encapsulation product from Example 1 | 1.45 | — | 0.50 |
| Encapsulation product from Example 2 | — | 1.15 | 0.50 |

The chewing gums of formulation (I) were shaped as strips, and those of formulations (II) and (III) as pellets.

Example F2

Sugar-Free Hard Caramels with Encapsulation Products According to the Invention

| Constituent | A (wt. %) | B (wt. %) |
|---|---|---|
| Palatinite, Type M | ad 100% | ad 100% |
| Water | 24.82% | 24.82% |
| Peppermint aroma | 0.15% | 0.05% |
| Orange aroma | — | 0.10% |
| Hesperetin | — | 0.01% |
| Spilanthol | — | 0.01% |
| Trans-pellitorine | 0.01% | — |
| Encapsulation product from Example 2 | 0.75% | 0.50% |

Palatinite was mixed with water and the mixture melted at 165° C. and then cooled to 115° C. Aroma and encapsulation product according to the invention, and trans-pellitorine in case A and spilanthol and hesperetin in case B, were added and after thorough mixing the mixture was poured into molds, then removed from the molds after solidification and individually packaged.

Example F3

Low-Fat Yogurts with Encapsulation Products According to the Invention

| | Preparation (values stated in wt. %) | | |
|---|---|---|---|
| Constituent | A | B | C |
| Sucrose | 10% | 8% | 6% |
| Tagatose | — | — | 0.5% |
| Fructose | — | — | 0.5% |
| Hesperetin | — | 0.01% | 0.005% |
| Phloretin | — | — | 0.005% |
| Peach aroma | 0.30% | — | 0.40% |
| Strawberry/rhubarb aroma | — | 0.25% | — |
| Encapsulation product from Example 1 | 0.25% | 0.90% | 0.40% |
| Encapsulation product from Example 2 | 0.40% | — | 0.50% |
| Yogurt, 0.1% fat | ad 100% | ad 100% | ad 100% |

The ingredients were mixed and cooled at 5° C.

Example F4

Low-Fat Yogurts with Encapsulation Products According to the Invention

| | Preparation (values stated in wt. %) | | |
|---|---|---|---|
| Constituent | A | B | C |
| D-Tagatose | 0.482% | 0.482% | 0.482% |
| Sucralose | 0.003% | 0.003% | 0.003% |

-continued

| Constituent | Preparation (values stated in wt. %) | | |
|---|---|---|---|
| | A | B | C |
| Aspartame | 0.005% | 0.005% | 0.005% |
| Acesulfame K | 0.01% | 0.01% | 0.01% |
| Hesperetin | — | 0.01% | 0.005% |
| Phloretin | — | — | 0.005% |
| Raspberry/lemon aroma | 0.30% | — | 0.40% |
| Strawberry/rhubarb aroma | — | 0.25% | — |
| Encapsulation product from Example 1 | 0.25% | 0.90% | 0.40% |
| Encapsulation product from Example 2 | 0.40% | — | 0.50% |
| Yogurt, 0.1% fat | ad 100% | ad 100% | ad 100% |

The ingredients were mixed and cooled at 5° C.

Example F5

Diet Chocolate Based on Fructose with Encapsulation Products According to the Invention A chocolate suitable for diabetics was produced from the following ingredients and poured into rectangular slabs:

Cocoa mass, fructose, skim-milk powder, cocoa butter, inulin, clarified butter, emulsifier soy lecithin, walnuts, table salt, vanilla yogurt aroma (containing vanillin and 1 wt. % of hesperetin, relative to the total weight of the vanilla aroma) and 1 wt. % of encapsulation product according to the invention from Example 1.

Nutritional Value (per 100 g):

protein 8.8 g, carbohydrates 34 g (of which fructose 23 g, lactose 7.5 g, sucrose 1.4 g), fat 36 g; fibre 18.5 (of which 12.2 g inulin); Sodium: 0.10 g. Cocoa content at least 50 wt. %.

Example F6

Muesli Mixture with Encapsulation Products According to the Invention

| No. | | A (wt. %) | B (wt. %) | C (wt. %) |
|---|---|---|---|---|
| 1 | Porridge oats | 17.00 | 17.00 | 17.00 |
| 2 | Crisp porridge oat clusters | 10.00 | 10.00 | 10.00 |
| 3 | Rice Crispies | 16.90 | 16.90 | 16.90 |
| 4 | Cornflakes | 16.50 | 16.50 | 16.50 |
| 5 | Currants | 3.50 | 3.50 | 3.50 |
| 6 | Hazel nuts, chopped | 2.50 | 2.50 | 2.50 |
| 7 | Glucose syrup from wheat, DE 30 | 9.50 | 9.50 | 9.50 |
| 8 | Sucrose | 19.00 | 19.00 | 19.00 |
| 9 | Water | 4.00 | 4.00 | 4.00 |
| 10 | Citric acid powder, anhydrous | 0.10 | 0.10 | 0.10 |
| 11 | Encapsulation product from Example 1 | 1.00 | — | 0.50 |
| 12 | Encapsulation product from Example 2 | — | 1.00 | 0.50 |

Mix constituents nos. 1 to 6 in a rotary drum (mix 1). Heat constituents nos. 7 to 9 and add constituents nos. 10 to 12 (mix 2). Add mix 2 to mix 1 and mix well. Finally, place the resultant muesli mixture on a baking sheet and dry in an oven for 8 minutes at 130° C.

Example F7

Fruit Gums with Encapsulation Products According to the Invention

| Ingredients: | A (wt. %) | B (wt. %) |
|---|---|---|
| Water | 22.70 | 24.70 |
| Sucrose | 34.50 | 8.20 |
| Glucose syrup, DE 40 | 31.89 | 30.09 |
| Iso Syrup C* Tru Sweet 01750 (Cerestar GmbH) | 1.50 | 2.10 |
| Gelatin 240 Bloom | 8.20 | 9.40 |
| Polydextrose (Litesse ® Ultra, Danisco Cultor GmbH) | — | 24.40 |
| Yellow and red coloring | 0.01 | 0.01 |
| Citric acid | 0.20 | 0.10 |
| Orange aroma | — | 0.10 |
| Encapsulation product from Example 1 | 1.0 | 0.90 |

Example F8

Chewable Candy with Encapsulation Products According to the Invention

Ingredients List:

| Water | | 7.7% |
|---|---|---|
| Sugar | refined sugar C4 | 41.0% |
| Glucose syrup | dextrose 40 | 37.3% |
| Hardened vegetable fat | melting point 32-36° C. | 6.6% |
| Lecithin | emulsifier (soy lecithin) | 0.3% |
| Gelatin | pig gelatin | 0.8% |
| Fondant | type S30 | 4.9% |
| Encapsulation product from Example 1 | | 1.4% |

Example F9

Fruity Muesli Bars with Encapsulation Products According to the Invention

Ingredients List:

| Sucrose | sugar | 16.0% |
|---|---|---|
| Glucose syrup | | 14.0% |
| Sorbitol P 300 | humectant | 5.0% |
| Vegetable fat | | 5.0% |
| Water | | 3.0% |
| Porridge oats | | 13.3% |
| Oat flakes | oat extrudates | 10.0% |
| Cornflakes | | 5.5% |
| Rice Crispies | rice extrudates | 20.0% |
| Currants | | 5.0% |
| Encapsulation product from Example 1 | | 1.3% |
| Encapsulation product from Example 2 | | 1.7% |
| Citric acid, powder | | 0.2% |

Example F10

Fatty Wafer Filling with Encapsulation Products According to the Invention

Ingredients List:

| | | |
|---|---|---|
| Hard vegetable fat | melting point 33-35° C. | 40.0% |
| Confectioners' sugar | | 37.0% |
| Dextrose | grape sugar, anhydrous, microfine | 19.0% |
| Citric acid | | 0.3% |
| Encapsulation product from Example 1 | | 3.7% |

Manufacturing instructions: Adjust temperature of fat to room temperature/approx. 21° C. Finely sieve confectioners' sugar. Beat all ingredients, including aroma, in a Hobart laboratory stirrer.

Example F11

Madeira Cake with Encapsulation Products According to the Invention

Ingredients List/Basic Madeira Cake Recipe:

| | | |
|---|---|---|
| Wheat flour | type 405 | 16.90% |
| Wheat starch | | 4.90% |
| Sucrose | sugar, EC quality I | 20.20% |
| Common salt | | 0.14% |
| Potato flour | | 7.09% |
| Powdered egg yolk | | 1.84% |
| Baking powder | | 0.70% |
| Beating emulsifier | mono-diglycerides | 1.42% |
| Water | | 13.48% |
| Clarified fat | melting point approx. 34° C. | 14.89% |
| Eggs | | 17.02% |
| Beta-carotene, 1% solution | | 1.42% |

Manufacturing Instructions:

Adjust temperature of fat. Place all dry ingredients in mixing bowl of Hobart laboratory mixer. Then add clarified fat, water and eggs (egg weight approx. 60 g/unit). Finally add 3 wt. % of encapsulation product according to the invention (from Example 2) and beat for 1 minute at speed 1 and for 2 minutes at speed 3. Place dough in a baking pan and bake for 55 minutes at 180° C.

Example F12

Short Pastry Cookies (Industrial Quality) with Encapsulation Products According to the Invention Ingredients List:

| | | |
|---|---|---|
| Wheat flour | type 550 | 50.0% |
| Soft vegetable fat | melting point 24-26° C. | 19.0% |
| Confectioners' sugar | | 19.0% |
| Salt | | 0.4% |
| Ammonium bicarbonate | raising agent | 0.4% |
| Skim-milk powder | | 1.0% |
| Maltose syrup | DE 60.5 | 1.2% |
| Water | | 5.50% |
| Encapsulation product from Example 1 | | 3.50% |

Manufacturing Instructions:
a) Mix confectioners' sugar, maltose syrup, skim-milk powder and soft vegetable fat to a smooth mixture in the Hobart laboratory kneader at speed 1.
b) Dissolve the ammonium bicarbonate with some of the water and add the remaining water to a) and mix briefly.
c) Add the remaining ingredients with the encapsulation product from Example 1 to mixture a) and work to a smooth dough.
d) Roll out the dough with the rolling machine to a thickness of approx. 3 mm, optionally apply a pattern with a wooden stamp and cut out in the desired shape.
Final thickness of dough: approx. 2.6 mm; oven temperature: 200° C., baking time: 6 minutes.

Example F13

Snack Articles with Encapsulation Products According to the Invention

Basic Recipe for the Production of Snacks (Crackers):
wheat flour (60-63%), baking powder (1.0-1.5%), vegetable fat (6.0-6.5%), maltose syrup (2.0-2.5%), emulsifier (1.2-1.8%), ammonium bicarbonate (1.5-2.0%), spray-dried skim-milk powder (1.0-1.5%), fresh bakers' yeast (0.3-0.9%), table salt (0.3-0.6%), water (20.0-23.5%), encapsulation product according to the invention (0.25-2.0 wt. %), preferably an encapsulation product according to Example 1 or 2.

The onion aroma ZA of the following recipe was added to the basic recipe in a proportion of 0.1 to 2%, relative to the mass of the basic cracker recipe, and the cracker was then baked or deep-fried.
Onion Aroma ZA:
2-trans-hexenal (0.26%), leek oil (0.31%), allinate (0.39%), methyl propyl disulfide (0.51%), foetida oil (0.65%), dithiazine in vegetable triglyceride (1.28%), dimethyl trisulfide (1.28%), dipropyl disulfide (2.56%), dipropyl trisulfide (5.13%), propylene glycol (8.20%), onion oil (10.26%), triacetin (69.17%).

Example F14

Powdered Seasoning with Encapsulation Products According to the Invention

Powdered seasonings, for example for snacks, are produced using the following recipe.
Basic Recipe for the Production of Seasonings:
table salt (10-25%), carrier (for example whey powder) (40-60%), fillers (for example fat powder) (5-15%), taste enhancer (1.5-3.5%), auxiliaries (for example silica) (0.1-5%), cheese powder (10-30%), hydrolysed vegetable proteins (5-10%), yeast extract (5-15%), spices (1-5%), acidulants (for example citric acid) (0.1-1.0%), coloring (for example paprika extract) (0.1-1.0%), encapsulation product according to the invention (1-8 wt. %), preferably an encapsulation product according to Example 1 or 2.

Example F15

Cream of Leek Soup with Encapsulation Products According to the Invention

A cream of leek soup is produced according to the following recipe: milk fat component, Vana Crema (25-30%), potato starch (15-25%), milk sugar, lactose (18-22%), maltodextrin (10-12%), salt (7-9%), monosodium glutamate (2-4%), vegetable fat (2-4%), spinach powder (1-2%), citric acid powder (0.2-0.4%), leek powder (1-2%), freeze-dried pieces of leek (approx. 10×10 mm) (0.5-1.5%), vegetable stock powder (0.2-0.5%), curcumin extract (0.05-0.1%), encapsulation product according to the invention (0.25-2.0 wt. %), preferably an encapsulation product according to Example 1 or 2.

The leek aroma LA of the following recipe was added to the basic recipe in a proportion of 0.2 to 3 wt. % relative to the mass of the basic recipe.

Leek Aroma LA:
propanethiol (0.05%), 1% diallyl disulfide in vegetable triglyceride (0.10%), hexanal (0.15%), leek oil (0.20%), dipropyl trisulfide (0.40%), 2-trans-hexenal (0.60%), 1-pentene-3-ol (1.20%), allinate (allyl isothiocyanate) (1.60%), 3-cis-hexenol (1.71%), dipropyl disulfide (2.01%), vegetable triglyceride (91.98%).

Example F16

Seasoning Mixture for Potato Chips with Encapsulation Products According to the Invention

| Constituent | Recipe A |
| --- | --- |
| Sodium glutamate | 3.50 g |
| Cheese powder | 10.00 g |
| Garlic powder | 2.00 g |
| Whey powder | 38.86 g |
| Seasoning extract oil | 0.20 g |
| Paprika powder | 9.80 g |
| Common salt | 19.00 g |
| Tomato powder | 9.00 g |
| Dry aroma | 2.50 g |
| Silicon dioxide | 0.02 g |
| Vegetable oil | 0.02 g |
| Onion powder | 3.00 g |
| Cream aroma concentrate | 0.03 g |
| Cheese aroma | 0.03 g |
| Tomato aroma concentrate | 0.04 g |
| Encapsulation product according to Example 2 | 2.00 g |

6 g of the seasoning mixture were applied to 94 g of potato chips.

Example F17

White Sauce with Encapsulation Products According to the Invention

| Constituent | Recipe A | Recipe B |
| --- | --- | --- |
| Maltodextrin | 26.28 g | 26.28 g |
| Common salt | 6.25 g | 5.35 g |
| Sodium glutamate | 2.00 g | 2.00 g |
| Vegetable fat | 5.00 g | 5.00 g |
| Pepper, white | 0.02 g | 0.02 g |
| Onion powder | 1.50 g | 1.50 g |
| Pregelatinized corn starch | 30.00 g | 30.00 g |
| Fat powder | 27.70 g | 27.70 g |
| Encapsulation product according to Example 1 | 1.25 g | — |
| Encapsulation product according to Example 2 | — | 2.15 g |

1000 ml of hot water were poured onto 90 g of the sauce mixture and the mixture was stirred vigorously with a whisk.

Example F18

Brown Sauce with Encapsulation Products According to the Invention

| Constituent | Recipe A | Recipe B |
| --- | --- | --- |
| Starch | 39.00 g | 40.00 g |
| Maltodextrin | 33.00 g | 33.10 g |
| Common salt | 6.00 g | 4.5 g |
| Sugar coloring, spray-dried | 5.00 g | 5.00 g |
| Yeast extract powder | 3.00 g | 3.00 g |
| Sodium glutamate | 2.00 g | 2.00 g |
| Sugar | 0.50 g | 0.50 g |
| Fat powder | 5.00 g | 5.00 g |
| Tomato powder | 3.00 g | 3.00 g |
| Natural vegetable extract | 1.00 g | 1.00 g |
| Onion extract | 0.30 g | 0.30 g |
| Pepper extract | 0.10 g | 0.10 g |
| Dry aroma | 1.00 g | 1.00 g |
| Encapsulation product according to Example 1 | 1.10 g | — |
| Encapsulation product according to Example 2 | — | 1.50 g |

1000 ml of hot water were poured onto 90 g of the sauce mixture and the mixture was stirred vigorously with a whisk.

Example F19

Tomato Soup with Encapsulation Products According to the Invention

| Constituent | Recipe A | Recipe B |
| --- | --- | --- |
| Water | 50.20 g | 50.80 g |
| Vegetable oil | 5.50 g | 5.50 g |
| Tomato paste | 24.00 g | 24.00 g |
| Cream | 1.00 g | 2.50 g |
| Sugar | 2.00 g | 2.00 g |
| Common salt | 1.70 g | 1.10 g |
| Sodium glutamate | 0.40 g | 0.40 g |
| Wheat flour | 5.50 g | 5.50 g |
| Starch | 1.20 g | 1.20 g |
| Diced tomatoes | 7.50 g | 5.50 g |
| Encapsulation product according to Example 1 | 1.00 g | — |
| Encapsulation product according to Example 2 | — | 1.50 g |

The solid constituents were weighed out, mixed and added to water. The vegetable oil was apportioned and the tomato paste added. The mixture was brought to the boil while being stirred.

Example F20

Chicken Soup with Encapsulation Products According to the Invention

| Constituent | Recipe A | Recipe B |
| --- | --- | --- |
| Water | ad 100 g | ad 100 g |
| Starch | 1.50 g | 1.50 g |
| Yeast extract | 0.40 g | 0.40 g |
| Onion powder | 0.30 g | 0.30 g |
| Pepper | 0.03 g | 0.03 g |
| Garlic powder | 0.05 g | 0.05 g |
| Vegetable extract | 0.20 g | 0.20 g |
| Common salt | 1.00 g | 0.50 g |
| Chicken soup aroma | 0.15 g | 0.22 g |
| Vegetable fat | 0.50 g | 0.50 g |
| Chicken flesh | 7.00 g | 7.00 g |
| Soup vegetables | 14.50 g | 14.50 g |
| Noodles | 3.00 g | 3.00 g |
| Encapsulation product according to Example 1 | 1.00 g | — |
| Encapsulation product according to Example 2 | — | 1.50 g |

The solid constituents were weighed out, mixed and added to water. The chicken fat was added, as were chicken flesh, soup vegetables and noodles. The mixture was brought to the boil while being stirred.

Example F21

Instant Soup with Encapsulation Products According to the Invention, Cream of Leek Type

| Constituent | A | B |
| --- | --- | --- |
| Potato starch | 20.0 g | 21.0 g |
| Fat powder | ad 100 g | ad 100 g |
| Lactose | 20.0 g | 21.0 g |
| Maltodextrin | 11.73 g | 11.70 g |
| Common salt | 8.0 g | 8.0 g |
| Sodium glutamate | 3.0 g | — |
| Spinach powder | 2.0 g | 2.0 g |
| Green leek powder | 2.0 g | 2.0 g |
| Citric acid, in powder form | 0.3 g | 0.3 g |
| Hardened vegetable fat | 3.0 g | 3.0 g |
| Freeze-dried leek | 1.0 g | 1.0 g |
| Chicken aroma | 1.0 g | 1.0 g |
| Seasoning mixture, "green leek" type, powder | 2.0 g | 2.0 g |
| Seasoning mixture, "cooked onion" type | 0.6 g | 0.6 g |
| Yeast seasoning mixture, "Vegetable stock" type, powder | 0.3 g | 0.8 g |
| Curcumin extract | 0.07 g | 0.07 g |
| Encapsulation product according to Example 1 | 1.00 g | — |
| Encapsulation product according to Example 2 | — | 1.50 g |

100 ml of hot water were poured onto 5 g of the respective powder mixture, in order to obtain a ready-to-drink soup.

Example F22

Instant Soup with Encapsulation Products According to the Invention, Chicken Soup with Noodles Type

| Constituent | Recipe A | Recipe B |
| --- | --- | --- |
| Starch | 16.0 g | 17.2 g |
| Common salt | 7.0 g | 7.0 g |
| Sucrose, refined | 3.2 g | 3.2 g |
| Sodium glutamate | 3.2 g | — |
| Sodium inosinate/sodium guanylate in a ratio of 1:1 | 0.8 g | 0.8 g |
| Acid-hydrolysed vegetable protein | 8.0 g | 8.0 g |
| Fat powder | 2.0 g | 2.0 g |
| Vegetable fat, spray-dried | 1.0 g | 1.0 g |
| Freeze-dried chicken flesh, in pieces | 2.0 g | 2.0 g |
| Soup noodles | ad 100 g | ad 100 g |
| Maltodextrin | 12.16 g | 13.13 g |
| Chinese vegetables, freeze-dried | 4.6 g | 4.6 g |
| Chicken aroma | 8.0 g | 8.0 g |
| Riboflavine, food coloring | 0.04 g | 0.04 g |
| Encapsulation product according to Example 1 | 1.00 g | — |
| Encapsulation product according to Example 2 | — | 1.50 g |

5.0 g of the respective powder mixture were boiled for 10 minutes in 100 ml of water, to obtain a ready-to-drink soup.

Example F23

Seasoning Mixture with Encapsulation Products According to the Invention, "Pepper" Type

| Constituent | Recipe A | Recipe B |
| --- | --- | --- |
| Milk protein | 0.8 g | 0.8 g |
| Locust bean flour | 2.0 g | 2.0 g |
| Corn starch | ad 100 g | ad 100 g |
| Common salt | 14.0 g | 15.0 g |
| Paprika powder | 12.0 g | 13.0 g |
| Tomato powder | 12.0 g | 13.0 g |
| Sucrose | 4.0 g | 4.0 g |
| Garlic powder | 0.5 g | 0.5 g |
| Hardened vegetable fat | 8.0 g | 8.0 g |
| Fat powder | 10.0 g | 11.0 g |
| Sodium glutamate | 6.0 g | 1.0 g |
| Beetroot and paprika, food coloring | 2.0 g | 2.0 g |
| Aroma, "pepper" type | 2.0 g | 2.0 g |
| Aroma, "pizza" type | 1.2 g | 1.2 g |
| Aroma, "tomato" type | 0.4 g | 0.4 g |
| Extract of black pepper | 0.1 g | 0.1 g |
| Encapsulation product according to Example 1 | 1.00 g | — |
| Encapsulation product according to Example 2 | — | 1.50 g |

In each case 100 g of neck of pork was evenly sprinkled with in each case 1.7 g of preparations A and B and cooked.

Example F24

Bouillon with Encapsulation Products According to the Invention

| Constituent | Recipe A | Recipe B |
|---|---|---|
| Fat powder | 8.77 g | 8.77 g |
| Sodium glutamate | 8.77 g | 5 g |
| Yeast extract powder | 12.28 g | 12.28 g |
| Common salt | 29.83 g | 29.83 g |
| Maltodextrin | ad 100 g | ad 100 g |
| Natural vegetable extract | 3.07 g | 3.07 g |
| Encapsulation product according to Example 1 | 1.00 g | — |
| Encapsulation product according to Example 2 | — | 1.50 g |

1000 ml of hot water were poured onto 15 g of the respective powder mixture.

Example F25

Tomato Ketchup with Encapsulation Products According to the Invention

| Constituent | A (wt. %) | B (wt. %) |
|---|---|---|
| Common salt | 2 | 2 |
| Starch, Farinex WM 55 | 1 | 1 |
| Sucrose | 12 | 9.6 |
| Hesperetin, 2.5% in 1,2-propylene glycol | — | 0.2 |
| Double tomato concentrate | 40 | 40 |
| Glucose syrup, 80 Brix | 18 | 18 |
| Distilled vinegar 10% | 7 | 7 |
| Water | ad 100 | ad 100 |
| Encapsulation product according to Example 1 | 1.00 g | — |
| Encapsulation product according to Example 2 | — | 1.50 g |

The ingredients are mixed in the stated sequence and the finished ketchup is homogenized with the assistance of a stirrer, bottled and sterilized.

Example F26

Throat Candies with Liquid/Viscous Core Filling (Centre-Filled Hard Candy)

| | I (wt. %) | II (wt. %) |
|---|---|---|
| Mixture A (shell) (80% of the candies) | | |
| Sugar (sucrose) | 58.12 | 49.37 |
| Glucose syrup (solids content 80%) | 41.51 | 49.37 |
| Peppermint oil | 0.10 | 0.15 |
| L-Menthyl succinate | 0.07 | 0.10 |
| l-Menthol | 0.10 | — |
| Lemon oil | 0.10 | 0.10 |
| Citric acid | — | 0.91 |
| Total (shell): | 100 | 100 |
| Mixture B (core) (20% of the candies) | | |
| High fructose corn syrup (sugar solids content 85%, only 15% water) | 83.42 | 83.38 |
| Glycerol | 15.00 | 14.50 |
| Encapsulation product according to Example 2 | 1.00 | 1.50 |
| Lecithin | 0.02 | 0.02 |
| Cinnamon oil | — | 0.30 |
| *Eucalyptus* oil | 0.28 | — |
| Trans-pellitorine | 0.01 | — |
| Vanillyl alcohol n-butyl ether | — | 0.10 |
| Red dye, as 5% aqueous solution | 0.20 | 0.20 |
| Vanillin | 0.07 | — |
| Total (core): | 100 | 100 |

Candies with a liquid/viscous core were produced on the basis of the methods described in U.S. Pat. No. 6,432,441 (Example 1 therein) and those described in U.S. Pat. No. 5,458,894 or U.S. Pat. No. 5,002,791. The two mixtures A and B were separately processed to form bases for the shell (mixture A) or core (mixture B). When consumed by affected individuals, the filled throat candies obtained by means of coextrusion were effective against coughing, sore throat and hoarseness.

The invention claimed is:

1. An encapsulated *Vaccinium* fruit extract composition, comprising:
   a) 0.5-50.0 wt. % *Vaccinium* fruit extract, and
   b) 30-98.9 wt. % yeast cell autolysate, wherein the yeast cell autolysate comprises a fraction of water-insoluble constituents of the yeast cell autolysate, and a fraction of water-soluble constituents of the yeast cell autolysate,
   and wherein the yeast cell autolysate is a product of incomplete yeast autolysis.

2. The composition as claimed in claim 1, further comprising:
   a) 0.1-10.0 wt. % sodium chloride, and
   b) 0.1-10.0 wt. % residual water.

3. The composition as claimed in claim 1, wherein the *Vaccinium* fruit extract is an extract of berries selected from the group consisting of (*Vaccinium corymbosum, Vaccinium vitis*-idaea, *Vaccinium oxycoccos, Vaccinium macrocarpon, Vaccinium microcarpum, Vaccinium gaultheroides, Vaccinium uliginosum, Vaccinium membranaceum, Vaccinium parvifolium, Vaccinium arboreturn, Vaccinium reticulatum, Vaccinium myrtilloides*, and mixtures thereof.

4. The composition as claimed in claim 1, wherein the composition comprises anthocyans in amounts of 0.1-30 wt. % of dry solids of the composition.

5. The composition as claimed in claim 1, wherein the yeast cell autolysate is an autolysate of Ascomycete cells:
   of the Saccharomycetaceae family or
   of the Cryptococcaceae family,
   or a mixture of autolysates of two or more of these Ascomycetes.

6. The composition as claimed in claim 1, wherein the total ratio by weight of the water-insoluble to soluble constituents of the yeast cell autolysate is in a range of 0.1:1 to 9:1.

7. The composition as claimed in claim 1, wherein the composition is a pharmaceutical, nutritional or pleasureful composition.

8. A method of producing the encapsulated *Vaccinium* fruit extract composition of claim 1 comprising the steps:
   a) providing a *Vaccinium* fruit extract,
   b) providing a yeast cell autolysate comprising a fraction of water-insoluble constituents of the yeast cell autolysate and a fraction of water-soluble constituents of the yeast cell autolysate, wherein the yeast cell autolysate is a product of an incomplete yeast autolysis, and
   c) mixing the *Vaccinium* fruit extract with the yeast cell autolysate fractions and water at a temperature of between 0 and 60° C. for a period of less than 4 hours to produce the encapsulated *Vaccinium* fruit extract composition.

9. An encapsulated *Vaccinium* fruit extract composition comprising a yeast cell autolysate and a *Vaccinium* fruit extract, wherein the *Vaccinium* fruit extract composition comprises 0.5-50.0 wt. % *Vaccinium* fruit extract and 30-98.9 wt. % yeast cell autolysate, wherein the yeast cell autolysate is a product of incomplete yeast autolysis, and wherein a ratio of *Vaccinium* fruit extract release in an individual's stomach to that in an individual's intestine is 0.3:1 to 3:1.

* * * * *

UNITED STATES PATENT AND TRADEMARK OFFICE
CERTIFICATE OF CORRECTION

PATENT NO.        : 7,914,825 B2
APPLICATION NO.   : 12/186883
DATED             : March 29, 2011
INVENTOR(S)       : Sven Siegel et al.

It is certified that error appears in the above-identified patent and that said Letters Patent is hereby corrected as shown below:

In the Claims:

At column 26, claim number 3, line number 49, please remove "(" before *Vaccinium*.

At column 26, claim number 3, line number 53, "arboreturn" should be corrected to read: "arboretum.".

Signed and Sealed this
Thirty-first Day of May, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,914,825 B2 | Page 1 of 1 |
| APPLICATION NO. | : 12/186883 | |
| DATED | : March 29, 2011 | |
| INVENTOR(S) | : Sven Siegel et al. | |

It is certified that error appears in the above-identified patent and that said Letters Patent is hereby corrected as shown below:

In the Claims:

At column 26, claim number 3, line number 49, please remove "(" before *Vaccinium*.

At column 26, claim number 3, line number 53, "arboreturn" should be corrected to read: "arboretum".

This certificate supersedes the Certificate of Correction issued May 31, 2011.

Signed and Sealed this
Twenty-third Day of August, 2011

David J. Kappos
*Director of the United States Patent and Trademark Office*